United States Patent [19]

Meinema

[11] Patent Number: 4,858,615
[45] Date of Patent: Aug. 22, 1989

[54] CATHETER SENSOR AND MEMORY UNIT

[75] Inventor: Ate. J. Meinema, Roden, Netherlands

[73] Assignee: Sentron v.o.f., Roden, Netherlands

[21] Appl. No.: 227,435

[22] Filed: Jul. 29, 1988

Related U.S. Application Data

[63] Continuation of Ser. No. 830,900, Feb. 18, 1986, abandoned, which is a continuation of Ser. No. 439,517, Nov. 5, 1982, abandoned.

[30] Foreign Application Priority Data

Nov. 10, 1981 [NL] Netherlands ............. 8105084

[51] Int. Cl.⁴ .............. A61B 5/00; G01K 15/00; G01L 27/00
[52] U.S. Cl. .................... 128/668; 128/672; 128/673; 128/736; 128/748; 129/912; 73/1 R; 364/571.01
[58] Field of Search .......... 128/912, 668, 672, 673, 128/675, 736, 748; 73/1 R; 364/571

[56] References Cited

U.S. PATENT DOCUMENTS

| | | | |
|---|---|---|---|
| 3,720,199 | 3/1973 | Rishtoin et al. | 128/1 D |
| 4,179,745 | 12/1979 | Wuertele | 364/571 |
| 4,192,005 | 3/1980 | Kurtz | 364/571 |
| 4,198,677 | 4/1980 | Brunner et al. | 364/571 |
| 4,240,441 | 12/1980 | Khalil | 128/692 |
| 4,274,423 | 6/1981 | Mizuno et al. | 128/695 |
| 4,303,984 | 12/1981 | Houvig | 364/571 |
| 4,323,972 | 4/1982 | Winter | 364/482 |
| 4,407,298 | 10/1983 | Lentz et al. | 128/713 |
| 4,418,392 | 11/1983 | Hata | 364/571 |
| 4,446,715 | 5/1984 | Bailey | 364/571 |

FOREIGN PATENT DOCUMENTS 0010762 5/1980 European Pat. Off. .
1532362 11/1978 United Kingdom .
2065890 7/1981 United Kingdom .

*Primary Examiner*—Lee S. Cohen
*Assistant Examiner*—John C. Hanley
*Attorney, Agent, or Firm*—Henry W. Collins; Thomas R. Vigil

[57] ABSTRACT

The sensor and memory unit (30, 92 or 94) includes a sensor assembly (34) having at least one sensor (48, 50 or 96) therein and a memory (18, 22, 70, 98) associated and fixed therewith. In one embodiment the memory (70, 98) is mounted in a memory module (38 or 90) which is connected by a multiconductor lead (40 or 88) to the sensor or sensors (48, 50 or 96). Also the sensor assembly (34) can be fixed in the distal end (36) of a catheter (32).

The sensor and memory unit (94) can be coupled to signal processing and conditioning circuitry (76, 176 or 276) which can include a microprocessor (178) for processing the sensor (96) signals and conditioning/correcting same based upon the information data retrieved from the memory (98).

2 Claims, 6 Drawing Sheets

FIG. 1
*PRIOR ART*
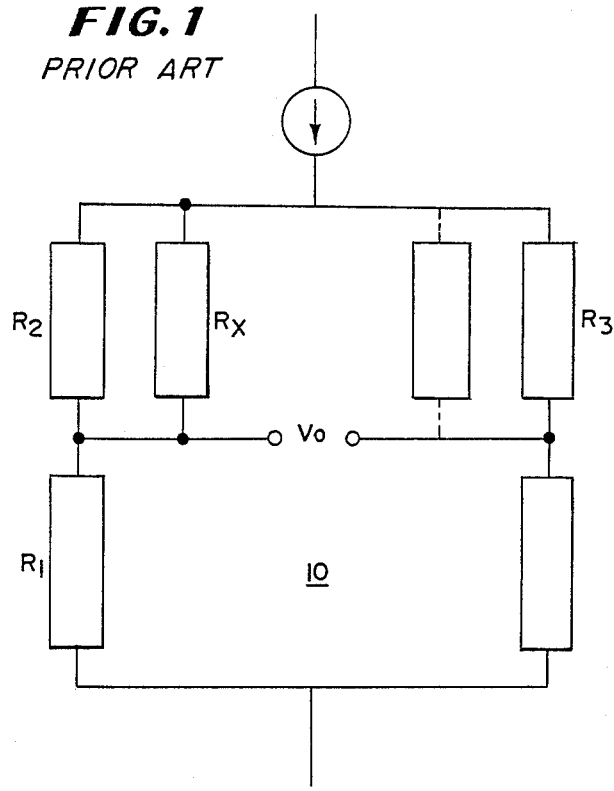
FIG. 2
*PRIOR ART*
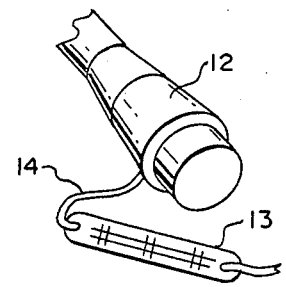
FIG. 3
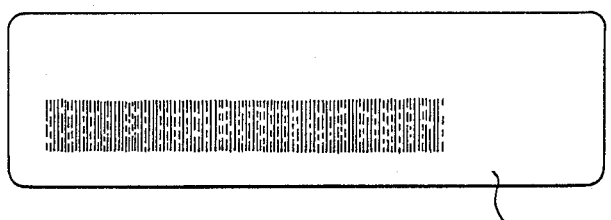
FIG. 4
| R | BINARY CODE VALUE |
|---|---|
| 10 | 0001 |
| 20 | 0010 |
| 30 | 0011 |
| 40 | 0100 |
| 50 | 0101 |

CATHETER SENSOR AND MEMORY UNIT

This is a continuation of application Ser. No. 06/830,900, filed Feb. 18, 1986, abandoned, which was a continuation of Ser. No. 439,517, filed Nov. 5, 1982, also abandoned.

BACKGROUND OF THE INVENTION

1. Field of the Invention

The present invention relates to a sensor and memory unit and more specifically to a catheter sensor and memory unit for monitoring a chemical, physical, or biological parameter and for providing a standard output. The unit includes a non-uniform sensor in a catheter and a memory connected thereto and, containing-correction information which is supplied in parallel with the sensor output to signal conditioning and processing circuits to produce a standard output for the parameter(s) sensed.

2. Description of the Prior Art

Sensors or sensor combinations that provide an electrically processable output signal are used in many fields for measuring and/or detecting a variety of phenomena. These phenomena may, for example, be of a chemical, physical or biological nature. As used herein, the term sensor can include a combination of co-operating sensors.

In the mass manufacture of sensors, an almost unavoidable problem is encountered in that, from one specimen sensor to another, the sensors have slightly different properties and exhibit a different behavior. This renders it difficult to compare accurately the results of measurements made with different sensors.

This drawback has been overcome in some instances by either applying very high standards in the production of the sensors, carrying out a very strict selection after production, and/or calibrating each sensor before use. These methods are time consuming, either on the side of production or on that of the consumer, and expensive.

An user of a sensor who is aware of the problem of the different response characteristics of different sensors will try to use the same sensor all the time after it has been calibrated. This, however, is often impossible in the field of medical sensors since certain sensors can only be used once and/or have to be replaced after several uses thereof to avoid infection to a patient which can occur if a sensor is sterilized more than a few times.

Also, heretofore, a sensor which can be easily calibrated before use has not been readily available.

Furthermore, the response characteristics of one and the same sensor may vary in time, as a result of inherent aging effects and/or as a result of its exposure to ambient conditions, such as temperature and pressure.

Heretofore attempts have been made to developed an "ideal" sensor in order to eliminate the above drawbacks. However, it is practically impossible to produce an "ideal" or perfect sensor and this is especially so in the case of sensors which must be mass produced in large numbers.

Additionally, it has been proposed to provide each sensor with an identification plate, chained, for example, to the sensor, and showing some characteristics of the sensor. The user can then correct the sensor's output signals by means of the data on the identification plate. Such correction may be effected, for example, by adjusting an electrical circuit arrangement which processes the sensor signals. This can be done, for example, by adjusting a potentiometer or thumb-wheel switches to effect the desired correction in the electrical circuit. This method is used, for example, in Fleisch Flow Transducers.

However, this method is not always effective since errors may occur in correlating a plate with a sensor, both during production, because, for example, the identification plates may be interchanged, and in use, because an identification plate is misread or the electrical circuit is maladjusted.

Such interchange of identification plates is not an uncommon event and periodically occurs in the mass production of sensors.

Furthermore, the adjustment of an electrical circuit by hand is a cumbersome job and lowers the market appeal of such sensors provided with identification plates.

In some sensor applications, such as, for example in the medical field, it is of great importance that the risk of error be as low as possible. As a result, manual adjustment of equipment coupled to sensors on the basis of data on an identification plate is highly undesirable.

Furthermore, even if manufacturing techniques are perfected to such an extent that certain types of sensors can be made sufficiently "ideal", it is yet often desirable to record specific unique information associated with a particular sensor in such a manner that when the sensor is used such unique information is immediately available without the risk of errors.

Such unique information may comprise, for example, the type of sensor, or type number, serial number, date of production, or safe use life of the sensor.

Consequently, an identification plate sensor combination as described above although useable in the medical field, still has the inherent drawbacks described above.

Still further it has been proposed in U.K. patent application No. 2,065,890 for: SENSOR SYSTEM WITH NON-LINEARITY CORRECTION by Felix J. Houvig, published July 1, 1981 to provide a sensor system comprising a fluid tight housing having a fluid pressure inlet portion and the sensor is mounted to an electronic component housing for electronic circuitry including sensor amplifying circuits, a power supply, a transistor switch, a shift register and a PROM. A signal isolation interface circuit is fixed to one side of the electronic component housing for connecting the electronic component housing and electronic circuitry therein to a microprocessor.

The PROM in this sensor system is programmed with correction control data to compensate for non-linearity and/or, perhaps, other characteristics in the sensor output.

As will be described in greater detail hereinafter, the sensor and memory unit of the present invention differ from the sensors or sensor systems described above by providing an integral, unitary sensor and memory combination unit where information regarding the characteristics of the sensor or sensor-memory combination are permanently recorded in the memory and the sensor and memory are indissolubly coupled together. The recorded information can be automatically and directly read and retrieved by separate electronic processing circuitry.

Also the sensor and memory unit of the present invention preferably includes a catheter for carrying the sensor therein, such as at one end thereof, and for providing a conduit for wire conductor connections between the sensor or sensors in the catheter and the memory fixed to the catheter. Such sensor and memory unit is particularly adapted for use in the medical field.

More specifically with respect to the sensor system disclosed in U.K patent application No. 2,065,890 such sensor system decribes a method for correcting an output signal of an electronic signal conditioning circuit where memory information may be used for non-ideal transducer characteristics, such as non-linearity, which is reflected in the output signal of the electronic signal conditioning circuit. However, an ideal linear transducer may have sensitivity deviation from nominal sensitivity specifications and the U.K. patent application No. 2,065,890 does not indicate how these differences in sensitivity from nominal specification can be treated.

As described in further detail hereinafter the sensor and memory unit of the present invention are utilized in a system where an ideal transducer is assumed, i.e., a perfectly linear transducer. However, all sensors built deviate from the nominal specification established therefor. In the memory of the present invention the actual specification of the ideal transducer (for example, pressure sensitivity, offset, temperature sensitivity) are stored.

In a sensor system including signal processing and conditioning circuitry that can be coupled to the sensor and memory unit of the present invention, the information data stored in the memory is decoded and the characteristics of the signal conditioning circuitry associated with the microprocessor are changed (for example, the amplification factor or offset are changed). As a result, the output signal from the signal conditioning circuitry always will be the same as for a sensor or transducer with nominal specification for any sensor and memory unit of the present invention that is coupled into the sensor system. Stated otherwise, the final output signal is standard for every transducer whereas in the sensor system disclosed in U.K. patent application No. 2,065,890, the amplitude of the signal depends on transducer sensitivity.

Also the memory can contain direct data for the adjustment of the signal processing and conditioning circuitry instead of data concerning the sensor characteristics.

Finally, and what has been explained above, the sensor and memory unit of the present invention is just that, namely a sensor and memory unit alone without any signal processing and conditioning circuitry, so as to provide a simple and single, compact unit which can be incorporated into a catheter for use in the medical field and which can be detachably coupled to any one of several types of signal processing and conditioning circuits.

SUMMARY OF THE INVENTION

According to the invention there is provided a catheter sensor and memory unit comprising a catheter, a sensor assembly mounted at the distal end of said catheter, and a memory module connected to the proximal end of said catheter and having a memory therein containing characteristic data of a sensor or sensors in said sensor assembly.

Also according to the invention there is provided an integral sensor and memory unit comprising a sensor assembly having one or more sensors mounted therein, a memory module having a memory mounted therein containing characteristic data for the sensor or sensors in said sensor assembly and a multiconductor lead connected between said sensor assembly and said memory module.

Further according to the invention there is provided a method for manufacturing sensors or sensor combinations that provide an electrically processable output signal, comprising the steps of: recording the characteristic data for each sensor or sensor combination in an automatically and directly electronically readable permanent memory; and indissolubly connecting the memory to the sensor or sensor combination.

Still further according to the invention there is provided a sensor or sensor combination that provides an electrically processable output signal combined with a directly and electronically readable permanent memory for recording the characteristic data of the sensor or sensor combination and means for indissolubly connecting the memory to the sensor or sensor combination.

BRIEF DESCRIPTION OF THE DRAWINGS

FIG. 1 is a schematic circuit diagram of a prior art sensor incorporated into a Wheatstone bridge.

FIG. 2 is a perspective view of a prior art sensor provided with an identification plate.

FIG. 3 is a plan view of a bar code defining the memory of one embodiment of a sensor and memory unit of the present invention.

FIG. 4 is a resistance/binary table defining the memory of a sensing and memory unit of another embodiment of the present invention.

DESCRIPTION OF THE PREFERRED EMBODIMENTS

Figure 5:
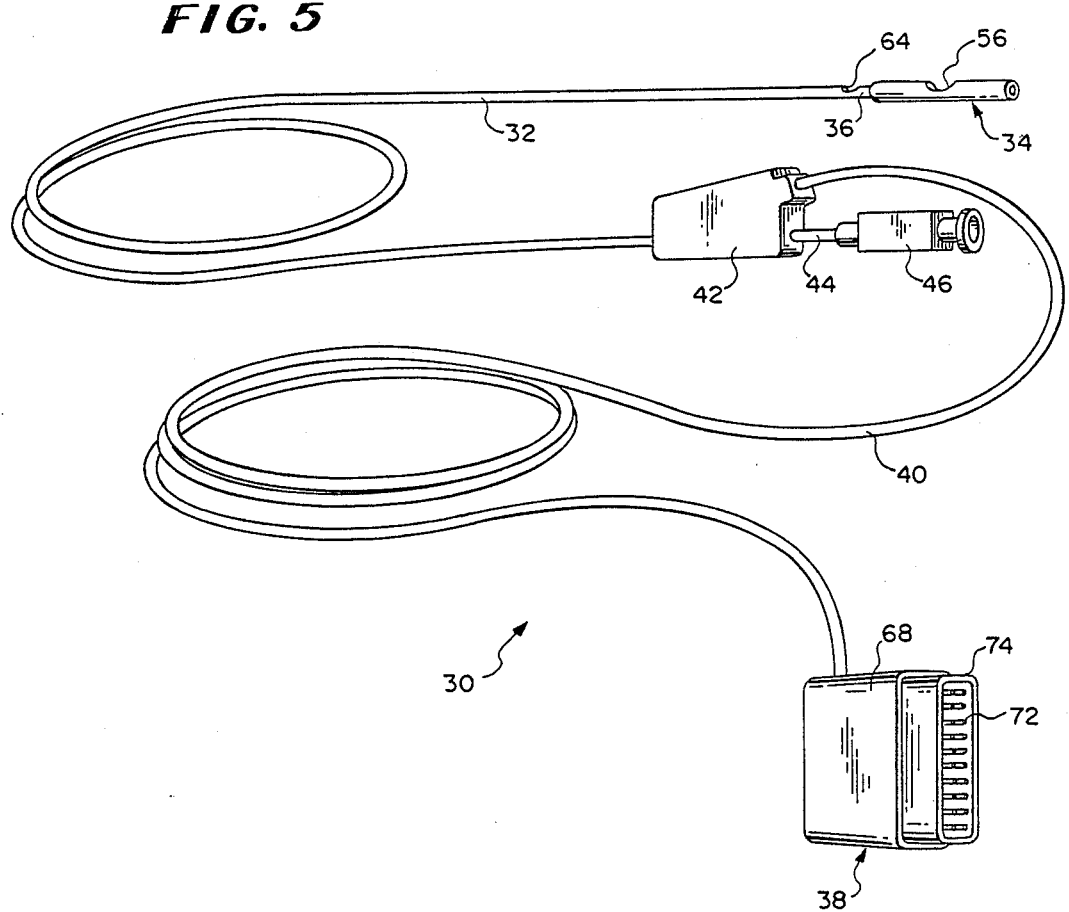
FIG. 5 is a perspective view of a catheter sensor and memory unit of still another embodiment of the present invention.

Referring now to the drawings in greater detail there is illustrated in FIG. 1 a Wheatstone bridge 10 comprising four resistors $R_1$ to $R_4$. These resistors form a sensor 10 which, for example, may be a pressure-sensitive sensor. Such circuit arrangements are well known.

According to known and conventional methods of production, an output voltage Vo is measured, and one or more suitable resistors $R_x$ are selected and mounted in the bridge 10, in order that bridge equilibrium and the sensitivity of the sensor 10 constituted by the bridge 10 may be adjusted in any desired way.

In this embodiment a series of sensors 10 are produced which, it is true, are all equal to the extent possible, but whose sensitivity are generally that of the sensor 10 having the lowest sensitivity.

The individual adjustment of each sensor 10 is expensive and time consuming, and in addition requires a large stock of resistors for the resistor $R_x$.

In FIG. 2 is illustrated a sensor 12 provided with an identification plate 13 which in the case shown is attached to the sensor by a cord or chain 14. The sensor 12 can be a Fleisch Flow Transducer. In the manufacture of such sensors 12, no effort is made to produce standard sensors 12. Instead, correction of the sensor 12 characteristics is done by the user. who adjusts equipment (not shown) for processing the output signals from a particular sensor 12 on the basis of the data carried by the identification plate 13 therefor. The disadvantages of this method of correction have been described above.

According to the teachings of the present invention, no attempt is made to produce sensors as uniform as possible by trimming or other adjustment. On the contrary, the characteristic properties of each sensor with regard to ambient effects, sensitivity and the like are measured. Such a measurement has been conventional in the past for purposes of quality control.

Further according to the teachings of the present invention, the resulting measurements and/or other data uniquely associated with the sensor are not specified on an identification plate, but joined with the sensor in such a manner that it is automatically processed by the equipment coupled to the sensor, without any initial adjusting operations being required from the user.

For this purpose, the measure data and/or other data are stored in a memory, the contents of which can be processed automatically and electronically. The memory is indissolubly connected to the associated sensor. For this purpose the memory may be incorporated, for example, in the sensor housing or in the sensor's connector. It is conceivable that, for certain uses, the memory is constituted by a specific configuration of, or specific connection of, connector pins, or by a specific mechanical treatment of the connector housing.

A special configuration of connector pins can be realized, for example, by placing the pins in a specific pattern and/or machining one or more pins house-key fashion.

The processing equipment then will include a complementary connector suitable for all possible configurations, and connected in such a manner that the information stored in the connector is processed in the proper manner. Alternatively, means for detecting the mechanical treatment of the connector housing are provided.

Moreover, a suitable memory can be realized, for example, by a magnetic card, a bar code marked on a carrier, a resistance code, or a PROM (programmable read only memory).

The processing equipment must, of course, be adapted to the type of memory being used. Such an adaptation, however, should not present any problems to those skilled in the art.

In FIG. 3 is shown an example of a bar code 18 embodying the characteristics of a sensor with which it is associated and for which it constitutes the memory of one embodiment of a sensor and memory unit constructed according to the teachings of the present invention. Such a bar code 18 is preferably marked on a connector housing, e.g., printed, engraved or impressed.

In FIG. 4 is shown a table 22 of resistance/binary code. Each resistor or combination of resistors R corresponds to a binary number specified in the table 22 stored in processing equipment. The processing equipment may comprise a microprocessor, which, under the control of the binary number associated with a given resistance code, effects certain corrections with regard to the sensor signal. The resistance/binary code may not be adequate, however, if a substantial amount of data concerning the sensor is to be stored, since large quantities of resistors must be kept in stock. For minimal data, however, the resistance code is quite suitable.

The use of a PROM as a memory appears to be very suitable. PROM's are commercially available with very small dimensions but with a relatively large memory capacity of 256 bits or more.

A PROM suitable for the purposes of the present invention is, for example the IM 5600-5610 series of Intersil, Inc.

During the production of sensors, a PROM can be automatically programmed by a computer-controlled testing system as used in the production of large numbers.

Furthermore, as stated before, the type of sensor and other unique information, such as type number, serial production date, safe service life, etc. can be recorded in the memory, which offers the possibility of designing processing equipment suitable for various types of sensors.

In this way there is provided with the sensor and memory in conjunction with a deciphering (microprocessor) circuit and signal conditioning circuit a multi-purpose measuring and detecting system which requires no user calibration thus enhancing its consumer appeal and which minimizes, if not altogether eliminates user errors in calibration and use. Also such a sensor and memory unit can readily be combined with a catheter to provide one preferred embodiment of the present invention, namely a catheter sensor and memory unit 30 as will now be described in detail in connection with the following description of FIGS. 5–12.

Referring now to FIG. 5 there is shown therein the catheter sensor and memory unit 30 which includes a catheter 32 a sensor assembly 34 at one end 36 of the catheter 32 and a memory module 38 coupled by a multiconductor lead 40 through a three way connector 42 to the other end 44 of the catheter 32. Also a coupling 46 is provided at the end 44 of the catheter 32 for coupling same to a fluid delivery or withdrawal system (not shown).

Figure 6:
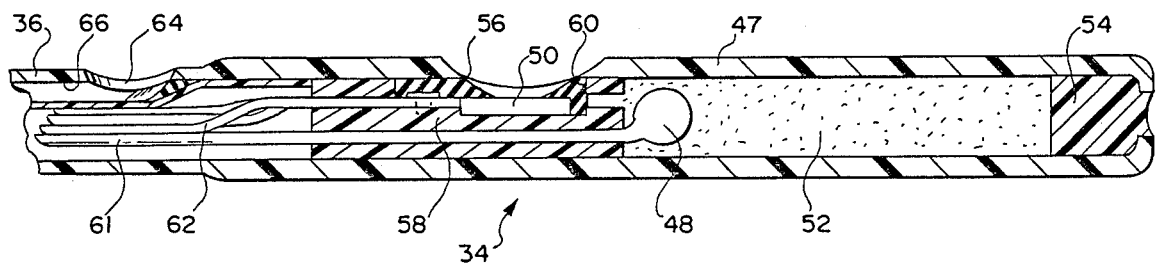
FIG. 6 is a sectional view of the sensor assembly at the end of the catheter shown in FIG. 5.

As shown in FIG. 6, the sensor assembly 34 includes a tube 47 having two sensors 48 and 50 therein. The sensor 48 is a temperature sensor bulb and the sensor 50 can be a pressure sensor or an electrode for in vivo measurement of body fluids. The temperature sensor bulb 48 is surrounded by thermal conducting material 52 packed in the end of the tube 47 which is sealed off by an end plug 54.

The tube 47 has a hole 56 therein for sensing pressure or for measuring body fluids. In this respect, inside the tube 47 is carrier 58 mounting the sensor or electrode 50 beneath the hole 56. A sealing material 60 is provided in the tube 47 around the sensor or electrode 50 and the hole 56.

Where body fluids are to be measured a membrane (not shown) formed of hydrogel can be positioned across the hole or aperture 56 so as to form an ion diffusion barrier between body fluids to be measured and electrolyte material within the tube 47 and in contact with electrode 50.

Several leads or insulated conductors such as conductor 61 from the temperature sensor bulb 48 and a conductor 62 from the sensor or electrode 50 extend rearwardly from the sensor assembly 34 through the catheter 32 to the three way connector 42 where the plurality of wire conductors 61 and 62 then branch off into the multiconductor cable 40 leading to the memory module 38.

In the distal end 36 of the catheter 32 there is provided and opening 64 which communicates with a passageway 66 within the catheter 32. This passageway 66 extends to and through the connector 42 through the proximal end 44 of the catheter 32 to the coupling 46 and facilitates the insertion or withdrawal of fluids through catheter 32 to or from the opening 64.

Where the sensor 50 is an electrode for measuring body fluids, the opening 64 can be positioned so as to open adjacent the membrane of hydrogel so that liquid exiting therefrom can provide a flushing action across the surface of the hydrogel membrane.

Figure 7:
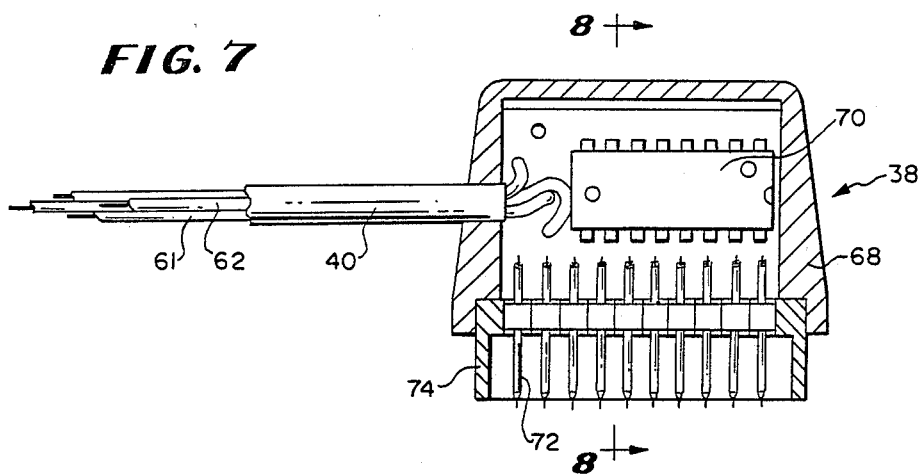
FIG. 7 is a sectional view of the memory module coupled to the catheter shown in FIG. 5.
Figure 8:
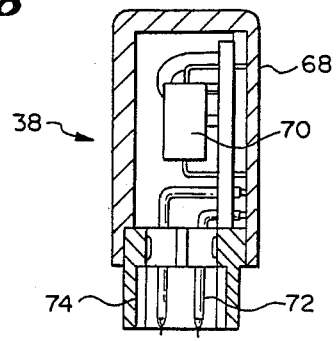
FIG. 8 is a sectional view of the memory module shown in FIG. 7 and is taken along line 8—8 of FIG. 7.

As shown in FIGS. 7 and 8, the multiconductor lead 40 extends to and into a housing. 68 of the memory module 38. As shown, a memory 70 such as a PROM is mounted within the housing 68 on a circuitboard. Wire conductors such as conductors 61 and 62 within the multiconductor lead 40 connect the sensors 48 and 50 to connector pins 72 situated within a connector housing 74 fixed to the housing 68. The PROM 70 is also connected to the connector pins 72.

Figure 10:
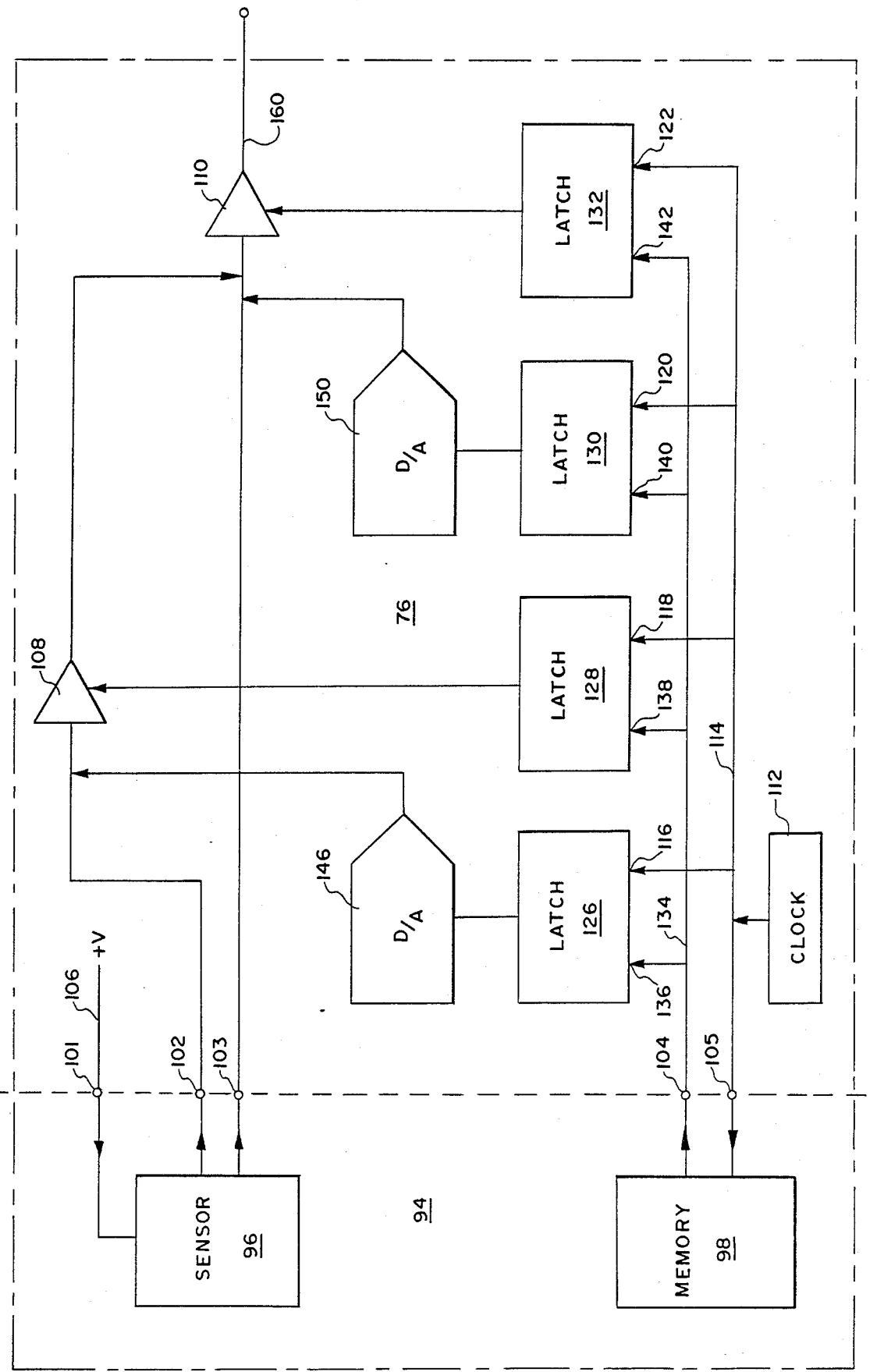
FIG. 10 is a schematic circuit diagram of one type of signal conditioning circuit to which a sensor and memory unit of the present invention can be detachably coupled to form a sensor system.

The connector pins 72 within connector housing 74 can then be easily connected to a mating connector socket module associated with signal processing and conditioning circuitry 76 (FIG. 10).

Figure 9:
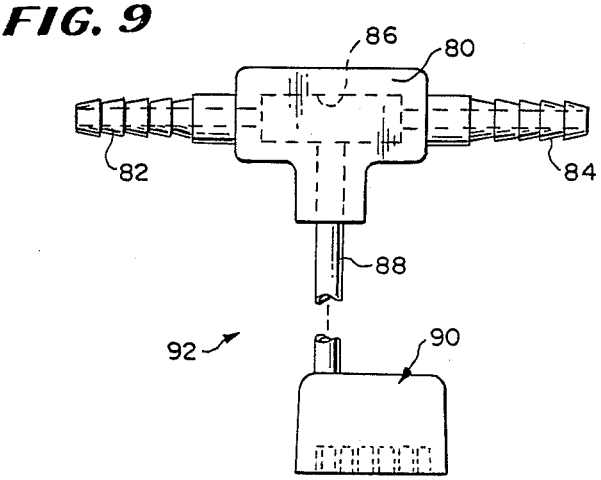
FIG. 9 is a plan view of an in-line pressure sensor, catheter and memory unit of yet another embodiment of the present invention.

In FIG. 9 is shown a three way coupling member or flow cell 80 which has in-line nozzles 82 and 84 on either side thereof and a sensing chamber 86 therein. The sensing chamber 86 has at least one sensor therein which is coupled by a lead 88 to a memory module 90 similar to or identical to the memory module 38 to form another embodiment of a sensor and memory unit 92 constructed in accordance with the teachings of the present invention. The sensor can be a flow rate sensor or a pressure sensor.

Referring now to FIG. 10 there is illustrated therein a signal processing and conditioning circuit 76 which is coupled to a sensor and memory unit 94 constructed in accordance with the teachings of the present invention and which for example can be the catheter sensor and memory unit shown in FIG. 5.

The sensor and memory unit 94 includes a sensor 96 and a memory 98. The circuit 76 is adapted to be coupled by means of connector pins 101-105 to the sensor and memory unit 94 as shown. The circuit 76 is adapted to measure and detect the characteristic data in the memory 98 associated with the sensor 96 and to process such data in the circuit 76.

The data is typically stored in digital form in the memory 98 associated with the sensor 96 and is converted in the signal processing and conditioning circuit 76 into voltages, currents or gain factors and such voltages, currents or gain factors are utilized in adjusting circuit components in the signal processing and conditioning circuit 76.

If the sensor and memory unit 94 is of the type illustrated in FIG. 5, the sensor 96 is housed or mounted within the distal end of a catheter. Electrical conductors within the catheter then connect the sensor 96 to connector pins 101-103 in a connector housing (not shown). The memory 98 associated with the sensor 96 can then be mounted in a connector housing (not shown) such as the housing 68 shown in FIG. 5 and connected to connector pins 104 and 105 as shown.

A voltage bus 106 is connected to connector pin 101 for supplying voltage to the sensor 96. If necessary, such voltage can also be supplied to the memory 98.

The sensor 96 can be of the type which will provide a temperature sensor signal to connector pin 102 and a pressure sensor signal to pin 103 which pins 102 and 103 are connected, respectively, to a first amplifier 108 and a second amplifier 110. As shown, the output of the amplifier 108 which receives the temperature sensor signal is combined with the pressure sensor signal supplied to the second amplifier 110 for controlling the adjustment of the second amplifier 110. Here we have temperature dependent pressure sensor signals and pressure dependent temperature sensor signals.

The adjustments of the amplifiers 108 and 110 are further controlled by the data read from the memory 98 and supplied to connector pin 104. This adjustment is effected by a clock 112. In this respect, the clock 112 is coupled via a bus 114 to the terminal pin 105 for supplying a clock pulse to the memory 98 connected to the connector pins 104 and 105.

As shown, the clock 112 supplies a clock pulse to the bus 114 which then supplies the clock pulse to the memory 98 and to clock inputs 116, 118, 120 and 122 of latching circuits 126, 128, 130 and 132. The data supplied to the connector pin 104 from the memory 98 is placed on a bus 134 which is connected to data inputs 136, 138, 140 and 142 of the latching circuits 126, 128, 130 and 132. As a result, each time a clock pulse is outputted by the clock 112, the data on the bus 134 from the memory is inputted to the respective latching circuits 126, 128, 130 and 132.

The latching circuits 128 and 132 then output a gain factor signal to the amplifiers 108 and 110 respectively as shown.

In a similar manner, the correction data clocked into the latches 126 and 130 are outputted to respective digital to analog converter circuits 146 and 150 which then output a bias or offsetting signal to the input of amplifiers 108 and 110 respectively as shown.

A corrected analog sensor signal then ultimately appears at output 160 of the second amplifier 110 and can be processed further in a suitable manner.

Figure 11:
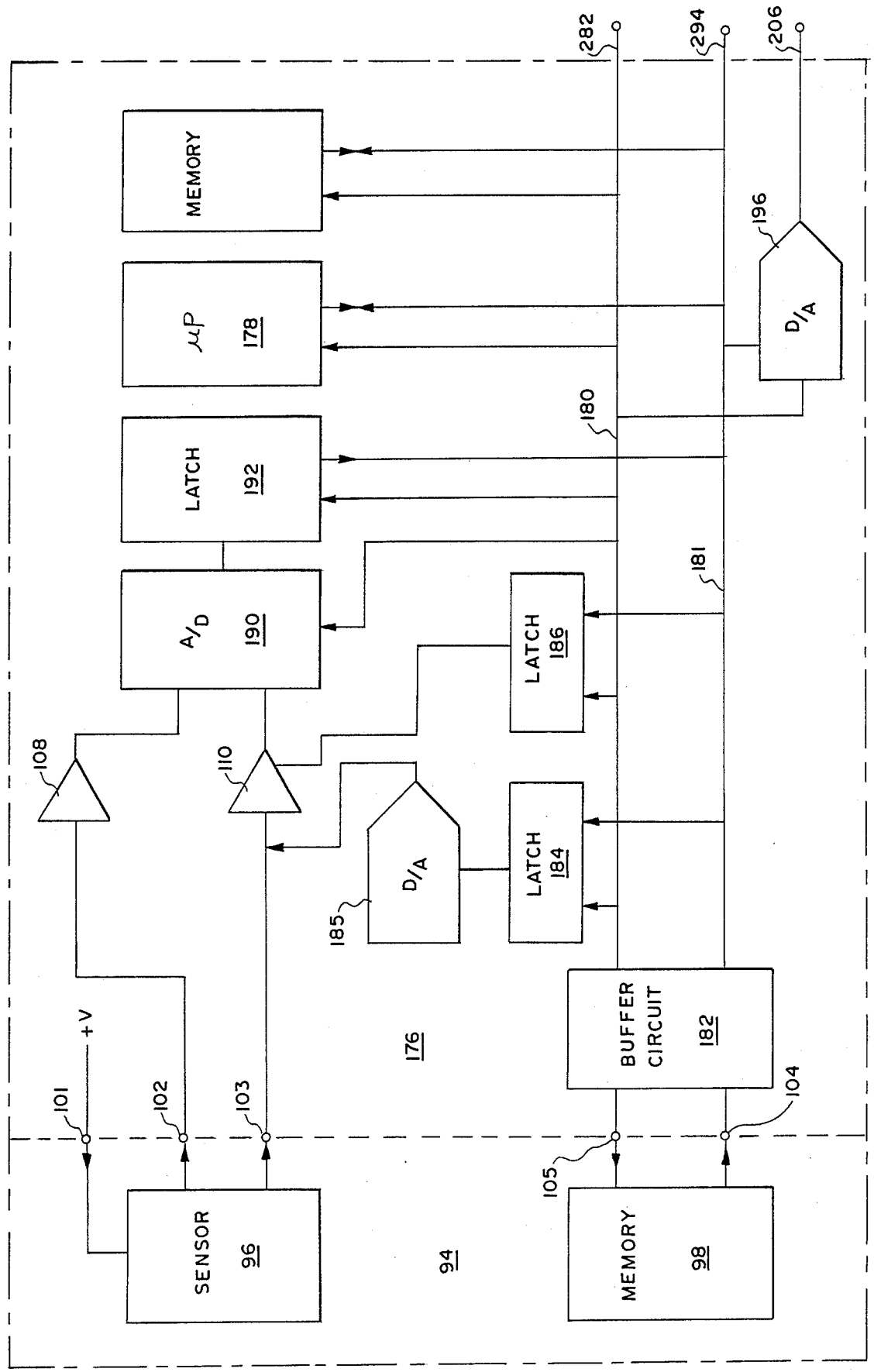
FIG. 11 is a schematic circuit diagram of another type of signal conditioning circuit to which a sensor and memory unit of the present invention can be detachably coupled to form a sensor system.

In FIG. 11 there is shown a different type of signal processing and conditioning circuit 176 which can be coupled to the sensor and memory unit 94 as shown. Here the circuit 176 includes a microprocessor 178 which is coupled by an address bus 180 and data bus 181 to a buffer circuit 182 that is connected to connector pins 104 and 105 for retrieving information data from the memory 98. The microprocessor 178 processes the data retrieved from the memory 98 and then causes appropriate adjustment of the second amplifier 110. In this respect, the microprocessor 178 supplies address signals to the address bus 180 which controls latch circuits 184 and 186. Latch circuit 184 supplies a digital signal to a D/A converter 185 which outputs an analog signal that is input to second amplifier 110 as an offset signal. The latch 186 supplies a gain adjust or gain factor signal directly to the second amplifier 110 as shown. The output signals from the amplifiers 108 and 110 are then digitized by an A/D converter 190 that has an output coupled to another latch circuit 192.

The microprocessor 178 will cause the latch circuit 192 to output a corrected digital sensor signal to the data bus 181. A D/A converter 196 is coupled to the address bus 180 and the data bus 181 and is operated by the microprocessor 178 to output at output 206 a corrected analog sensor signal converted from the signal supplied to the data bus 181 by the latch 192.

Figure 12:
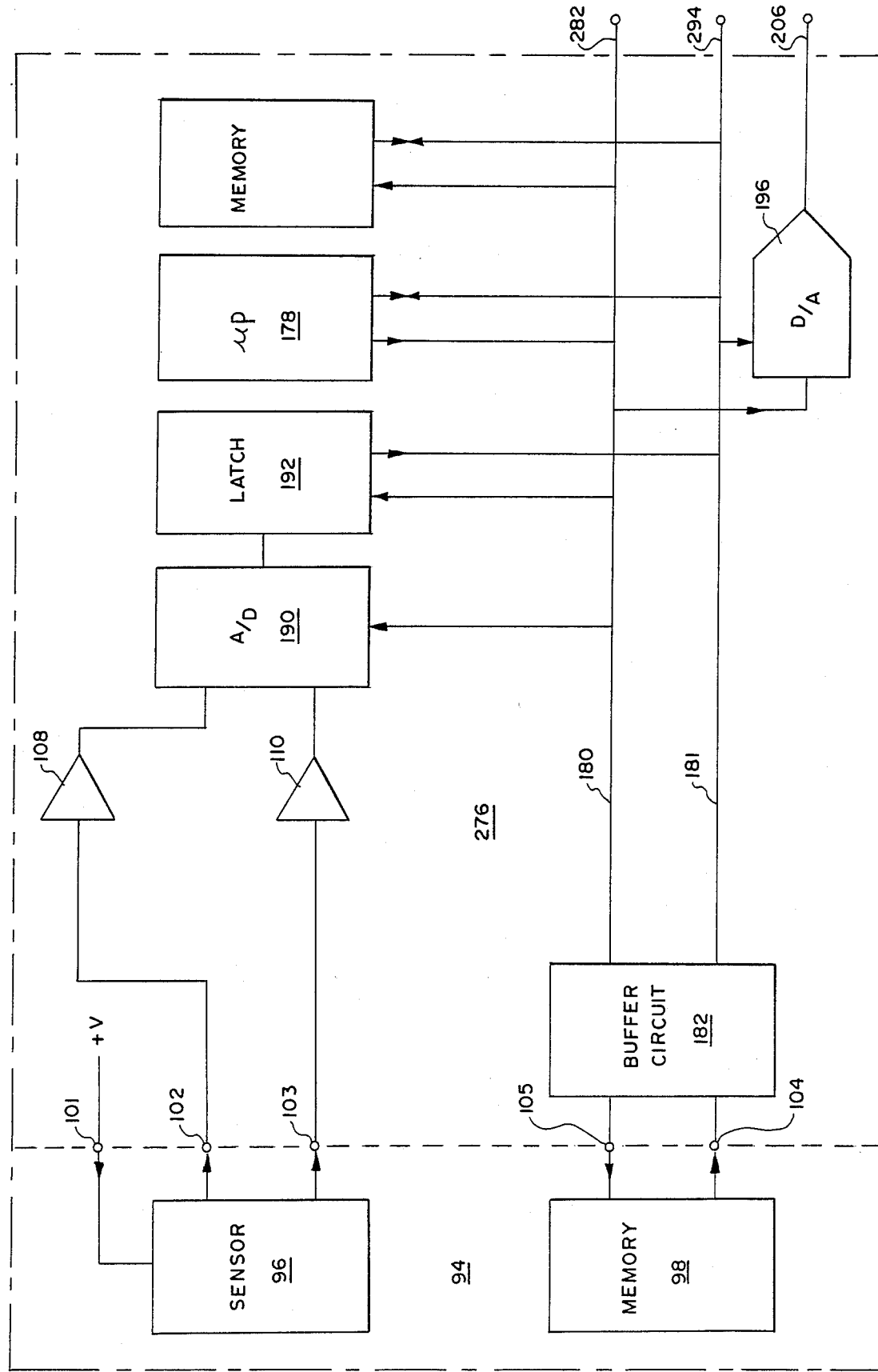
FIG. 12 is a schematic circuit diagram of still another type of signal conditioning circuit to which a sensor and memory unit of the present invention can be detachably coupled to form a sensor system.

Referring now to FIG. 12 there is illustrated therein a modified signal processing and conditioning circuit 276 which is similar to the circuit 176 except that in this circuit 276 the latches 184 and 186 and the D/A converter 185 are omitted and the amplifier 108 and 110 have a fixed amplification setting. In this modified circuit, the data stored in the memory 98 is not used by the microprocessor 178 for adjusting the settings of amplifier 110. Rather, the data stored are used as computational magnitudes for processing the sensor signal.

The information stored in the memory 98 can be utilized to process the sensor signals supplied to the amplifiers 108 and 110. Alternatively, the information data in the memory 98 can be passed directly to output terminals 282 and 294 as shown in FIGS. 11 and 12, after conversion, if necessary, into a form suitable for further processing, such as, for example, for being displayed on a display device (not shown).

It will be understood from the foregoing description that the teachings of the present invention can be utilized in different ways in a method for manufacturing sensors or sensor combinations together with the recording of characteristic data for individual sensor or sensor combinations in an automatically and directly electrically readable permanent memory. Also, according to this method, the memory is indissolubly connected to the sensor or sensor combination.

Obviously, the particular data stored, the magnitude to be corrected and the number of corrections will depend, of course, upon the particular sensor utilized. In this respect, the sensor or sensor combination can include a flow rate sensor, a pressure sensor, a temperature sensor, an electrolyte sensor or a chemical sensor.

Moreover, modifications can be made to the various embodiments of the present invention described above without departing from the teachings of the invention. For example, the chamber 86 within the three way coupling member 80 can have a flow rate sensor mounted therein instead of a pressure sensor.

Also it will be apparent that the sensor and memory unit of the present invention has a number of advantages, some of which have been described above and others of which are inherent in the invention. Specifically, the sensor and memory unit of the present invention can be disposable sensors, can be mass produced and can be utilized in the medical field or in the airplane industry. Accordingly, the scope of the invention is only to be limited as necessitated by the accompanying claims.

I claim:

1. A living body parameter sensing system including: a catheter sensor and memory unit; and, information and signal processing circuitry; said catheter sensor and memory unit including:
a catheter,
a non-ideal sensor mounted in said catheter,
a connector assembly including a connector housing,
said catheter being connected to said connector housing,
connectors mounted in said connector housing,
conductors in said catheter connected between said sensor and said connectors mounted in said connector housing, and
memory means for storing departure information data including offset and amplification data relative to the departure of non-ideal sensor output signals from ideal sensor output signals,
said memory means being mounted in said connector housing and being connected to said connectors such that said sensor and said memory means are permanently joined together by being mounted together in said catheter sensor and memory unit and by being connected to said connectors; said information and signal processing circuitry including:
means coupled to said memory means via said connector for retrieving the departure information data including offset data and amplification data relative to first sensor output signals from said memory means,
means coupled to said sensor via said connectors for retrieving first sensor output signals from said sensor relative to a first living body parameter,
means for offsetting said first sensor output signals retrieved from said sensor relative to the offset data for said first sensor output signals retrieved from said memory means,
means for amplifying said retrieved first sensor output signals,
means for adjusting the gain of said amplifying means relative to said amplification data for said first sensor output signals retrieved from said memory means, and
means coupled to said amplifying means for providing a first sensor output signal standardized for amplitude and offset.

2. The sensing system of claim 1, wherein said information and signal processing circuitry further includes:
second means for retrieving, from said sensor, second sensor output signals related to a second living body parameter which affects said first sensor output signals of said first living body parameter,
said memory means having departure information data including offset and amplification data relative to the departure of the non-ideal second sensor output signals from ideal second sensor output signals,
second means for retrieving said departure information data from said memory means including offset and amplification data relative to said second sensor output signals,
means coupled between said second means for retrieving departure information data from said memory means and said second means for retrieving second sensor output signals for offsetting said retriever second sensor output signals relative to said offset data for said second sensor output signals,
said second means for retrieving second sensor output signals including second amplifying means,
means for adjusting the output of said second amplifying means relative to said amplification data for said second sensor output signals retrieved from said memory means, and means for combining the second sensor output signals from said second amplifying means with the retrieved first sensor output signals supplied to said first amplifying means, whereby said means for providing said first sensor output signal provides a first sensor output signal which is also standardized relative to a standardized output signal for the second living body parameter which is standardized for amplitude and offset.

* * * * *